United States Patent [19]

Langley et al.

[11] Patent Number: 5,744,152
[45] Date of Patent: Apr. 28, 1998

[54] POLYMERIC COMPOSITIONS AND METHODS OF PRODUCING THEM

[75] Inventors: John Langley; Kenneth Charles Symes, both of West Yorkshire, Great Britain

[73] Assignee: Allied Colloids Limited, England

[21] Appl. No.: 373,397

[22] Filed: Jan. 17, 1995

Related U.S. Application Data

[63] Continuation of Ser. No. 193,906, Feb. 9, 1994, abandoned, which is a continuation of Ser. No. 896,840, Jun. 11, 1992, abandoned, which is a continuation of Ser. No. 398,088, Aug. 24, 1989, abandoned.

[30] Foreign Application Priority Data

| Aug. 24, 1988 | [GB] | United Kingdom | 8820061 |
| Aug. 24, 1988 | [GB] | United Kingdom | 8820062 |
| Jan. 19, 1989 | [JP] | Japan | 8901194 |

[51] Int. Cl.$^6$ ............................. A01N 25/10; A61K 9/16
[52] U.S. Cl. ............................. 424/408; 424/409; 424/438; 424/485; 424/487; 424/489; 424/497; 424/501; 424/94.6; 514/772.6; 428/402.24; 428/407; 264/4.1; 252/174.12; 427/213.31; 427/213.36
[58] Field of Search ............................. 424/408, 409, 424/438, 485, 487, 489, 497, 501, 94.6, 94.63, 94.67, 94.61; 514/772.6; 523/122, 160, 223, 342; 528/492, 501; 524/702, 704; 428/402.24, 407; 264/4.1, 4.33, 4.6, 4.7, 15; 252/1, 174.12; 427/213.31, 213.36

[56] References Cited

U.S. PATENT DOCUMENTS

| 3,492,398 | 1/1970 | Marco et al. | 424/438 |
| 3,584,113 | 6/1971 | Takebe et al. | 424/487 |
| 3,629,392 | 12/1971 | Banker et al. | 424/487 |
| 3,691,090 | 9/1972 | Kitajima et al. | 252/316 |
| 4,021,364 | 5/1977 | Speiser et al. | 252/316 |
| 4,037,040 | 7/1977 | Trapasso et al. | 526/88 |
| 4,411,754 | 10/1983 | Kaetsu et al. | 204/159.15 |
| 4,670,501 | 6/1987 | Dymond et al. | 524/458 |
| 5,387,622 | 2/1995 | Yamamoto | 523/902 |

FOREIGN PATENT DOCUMENTS

| 1214389 | 11/1986 | Canada . |
| 0102265 | 3/1984 | European Pat. Off. . |
| 0161038 | 11/1985 | European Pat. Off. . |
| 0227305 | 7/1987 | European Pat. Off. . |
| 8904170 | 5/1989 | WIPO . |

*Primary Examiner*—Neil S. Levy
*Attorney, Agent, or Firm*—Ostrolenk, Faber, Gerb & Soffen, LLP

[57] ABSTRACT

Release of an active ingredient can be controlled and the active ingredient can be protected from the environment during storage, by distributing it throughout a matrix containing a relatively large amount of polymeric material that is soluble and swellable in aqueous alkali but less soluble and swellable at a lower pH value and which is in the form of a dried oil-in-water emulsion of the polymer or a relatively insoluble partial salt of the polymer with a volatile amine, the full salt of the polymer being relatively soluble. The composition is of particular value for the protection of detergent enzymes.

11 Claims, No Drawings

POLYMERIC COMPOSITIONS AND METHODS OF PRODUCING THEM

This is a continuation of application Ser. No. 08/193,906, filed Feb. 9, 1994, now abandoned which was a continuation of application Ser. No. 07/896,840, filed Jun. 11, 1992, now abandoned, which was a continuation of application Ser. No. 07/398,088, filed Aug. 24, 1989, now abandoned.

It is well known to formulate an active ingredient (for instance an agricultural or pharmaceutical active material or a detergent enzyme) in the form of particles using a polymeric binder. For instance active ingredient may be distributed through a polymeric matrix which, in practice, generally contains a relatively large amount of inert filler.

If the binder is water soluble, ambient atmospheric moisture will readily permeate into the particles, and addition of the particles to water will result in rapid release of the active ingredient. There are many instances where it is desirable that, for instance, release should only occur when the particles are exposed to a predetermined pH environment and it is standard practice to apply a polymeric coating around the particles, the polymer being impermeable at one pH and permeable (or soluble) at another pH. Such coatings are, for instance, widely used as enteric coatings. An example is in WO88/06407 wherein the particles of a fungal active ingredient distributed in a matrix are provided with an enteric polymeric coating that will permit release of the fungus only at a predetermined pH. Another example is in EP 277532.

A problem with enteric coatings is that there is a risk that they may not provide an adequate barrier over the total area of every granule or tablet, either because of non-uniformity in the coating or because they are accidentally fractured after application. Thus active ingredient near the outside of the matrix is liable to be exposed to ambient conditions. When the matrix itself is accidentally fractured (as frequently happens due to the relatively low amount of protective polymer that is usually included in the matrix) then this results in exposure of further active ingredient to ambient conditions. Another problem arises when it is necessary to combine rapid release upon addition of the particles to suitable water with the need or thorough protection for the active ingredient from the ambient atmosphere during storage. For instance particles containing an enzyme for a detergent need to dissolve very rapidly upon the addition to wash liquor but need to prevent deactivation of the active ingredient (by migration of atmospheric moisture through the particles) during storage. If the protective outer coating is sufficiently impermeable to prevent deactivation of the enzyme by ambient moisture then the particles are liable to dissolve only very slowly, while if the coating is sufficiently thin that the particles will dissolve fast then the coating is liable to provide an ineffective barrier to atmospheric moisture.

Additionally, it is undesirable to have to make the particles in two stages, the initial stage involving the formation of the matrix and the second stage involving the application of the protective coating to it.

Various ways are known for forming the initial matrix containing the active ingredient and around which the coating can be applied. For instance biologically produced active ingredients can typically be put into particulate form by spray drying a fermentation broth and aggregating the resultant powder using a polymeric binder that typically is soluble in water.

It would be desirable to be able to provide particles containing active ingredient wherein the particles give good protection to the active ingredient during storage of the particles (even if the particles are fractured) and yet will permit very rapid exposure of the active ingredient to different ambient conditions, for instance exposure to alkaline water.

In GB 1,353,317 an enzyme is precipitated from its solution by the addition of a relatively very small amount of anionic polymer, followed by collection of the resultant precipitate and drying. However the amount of polymer would be much too low to protect the enzyme or control its release.

A particular situation arises when it is desired to formulate a pesticidally active veterinary composition that is to be eaten by livestock and expelled from the livestock in its faeces, the active ingredient then exerting its pesticidal activity only in the faeces. Because of the nature of the active ingredient, it is generally necessary to minimise the risk of release of any active ingredient as it passes through the gastro intestinal tract of the livestock.

A particulate composition according to the invention comprises particles comprising an active ingredient distributed substantially uniformly throughout a matrix comprising polymeric material, and the amount of polymeric material is at least 0.5 times the weight of active ingredient and is at least 50% of the weight of the matrix, the polymeric material is swellable in water at pH above 7, and the polymeric material of the matrix, at least in the outer surface of the matrix, is substantially less swellable in water at a lower pH, and the matrix has been formed by drying either an oil-in-water emulsion of the polymer or a solution of a salt of the polymer with a volatile amine that has been partially or wholly evaporated during the drying (at least from the outer surface of the matrix). The polymer in the particles includes carboxylic or other suitable anionic groups wholly or mainly in free acid form and the polymer can subsequently be rendered more soluble in water by conveting them to alkali-metal or amine salt form.

The invention has a number of advantages. One advantage is that the protection and release proterties are provided by the use of the matrix polymer itself, and so it is not necessary to subject the particles to a separate coating step. Another advantage is that, since it is unnecessary to provide an enteric coating, it does not matter if the particles are subjected to friction or other forces that would be liable to fracture the protective coating that, prior to the invention, would have been provided around the matrix. Another advantage is that, if the particles are fractured, the high polymer content means that only a relatively small amount of the active ingredient will be exposed to the ambient conditions. Naturally, improved results are achieved, from this point of view, when the amount of polymer is well above the minimum specified above. As explained below the amount of polymer is generally at least 7 times the amount of active ingredient and the polymer generally constitutes at least 90% of the matrix.

In addition to requiring the use of this unusually large amount of polymer, the Invention also requires that the polymer shall have been introduced in one of two forms.

In one form the polymer is initially introduced as a solution of a water soluble salt with a volatile amine of a polymer that is relatively insoluble and non-swelling in acid and throughout which the active ingredient is dispersed or dissolved, and the solution is heated to form the dry matrix and to volatilise the amine and thereby form a polymer that is insoluble in acid. The preferred volatile amine is ammonia.

In another form, the polymer is initially introduced as an emulsion of film forming polymeric material throughout which the active ingredient is subtantially uniformly dispersed or dissolved and the emulsion is then dried to form the dry matrix, the polymeric material being film forming at the drying temperature or at a lower temperature.

As explained in more detail below, the drying can be by spray drying the aqueous phase containing the active ingredient and the dissolved or emulsified polymer. This method has the advantage that it can be operated by the conventional spray drying techniques modified by the use of the special polymer. Alternatively, and preferably, the drying is by dispersing the aqueous phase containing active ingredient and dissolved or emulsified polymer into a water immiscible liquid and azeotroping to form substantially dry beads or substantially dry particles dispersed in the immiscible liquid.

It is particularly surprising that it is possible and useful to obtain polymeric matrix particles under these circumstances. Thus in one instance the dispersed polymer particles are the ammonium or other volatile amine salt of the polymer before the azeotroping, but some or all of the polymer is converted to the free acid salt during the azeotroping. In the other system, the aqueous polymer phase that is dispersed in the non-aqueous liquid is itself an emulsion of polymer in water.

The final matrix is homogeneous in the sense that the polymeric material provides a continuous phase throughout the matrix. This minimises the risk of fracture of beads or tablets of the composition. Generally the polymeric material constitutes at least 50%, preferably at least 75% and most preferably at least 90% by weight of the solid composition formed of the matrix, active ingredient and any inert material distributed through the matrix.

The amount to polymeric material must be sufficient to form the matrix and is preferably at least twice the amount (by weight) of active ingredient. Generally it is at least 7 times and usually at least 10 times the amount of active ingredient. It is usually unnecessary for it to be more than 50 times the amount of active ingredient and suitable amounts are generally in the range 15 to 30 times the amount of active ingredient. As a result of having this relatively large polymeric content, the active ingredient is present in a relatively dilute state within the matrix and so if there is any physical damage to the matrix the amount of active ingredient that is exposed to the environment is low.

The active ingredient can be included in a solution or emulsion of monomeric material that is then polymerised, in the presence of the active ingredient, to form the solution or emulsion of film forming polymeric material. Preferably however the polymer is provided as a solution or emulsion and the active ingredient is then combined with this preformed polymer solution or emulsion. The active ingredient can be dissolved or dispersed into the polymer solution or emulsion. The active ingredient must be distributed substantially uniformly through the solution or emulsion (and through the final matrix).

The polymer that is used should be film forming in the sense that the polymeric residue forms, during the process, a coherent mass of dry polymeric material when the solvent is removed from the solution or the continuous phase is removed from the emulsion. The glass transition temperature should therefore preferably be at or below the chosen distillation temperature and often it is below 40° C., frequently below 20° C.

At this stage of the process, the polymer can be insoluble in water in which event it is present as an emulsion that has been made by oil-in-water emulsion polymerisation. The emulsion should be such that the polymer particles are film forming, as described above, and if necessary the emulsion may include a plasticising additive that will render the polymer film forming. For instance a solvent or plasticiser for the polymer may be included in the emulsion in an amount sufficient to render the emulsion particles film forming.

When the polymer is present as an emulsion it may be a polymer that is cross linked sufficiently for the final matrix to be insoluble in all aqueous media but to be swellable in aqueous media of selected pH. Often however the polymer is linear and so is potentially soluble in aqueous media at selected pH values.

Suitable emulsion polymers are made by oil-in-water emulsion polymerisation of one or more ethylenically unsaturated monomers that are insoluble in the water phase of the polymerisation mixture. The monomers that are emulsion polymerised are a blend of anionic solubilising monomers and non-ionic monomers, the overall blend being insoluble at the pH of the emulsion. The emulsion polymerisation is conducted at a pH below 7 at which the monomer blend and the polymer is insoluble and non-swellable. The amount of solubilising ionic monomer will be such that the final polymer can be solubilised by exposure to the chosen alkaline pH but not at a lower pH.

The other monomers in the blend are non-ionic and have a solubility such that the blend is insoluble at the pH of the emulsion. They can include water soluble monomers such as (meth) acrylamide but generally they are all water insoluble monomers such as alkyl (meth) acrylates, styrene, acrylonitrile, vinyl chloride, vinyl acetate or vinyl butyl ether. Ethyl acrylate is preferred.

Suitable anionic monomers are ethlenically unsaturated carboxylic or sulphonic monomers, most preferably monomers such as (meth) acrylic acid, crotonic acid, itaconic acid, maleic acid, (meth) allyl sulphonic acid, vinyl sulphonic acid and 2-acrylamido-2-methyl propane sulphonic acid. Methacrylic acid is preferred.

The polymer is often formed from 10–70% methacrylic acid or other anionic monomer, 10–70% ethyl acrylate or other insoluble monomer and 0–70% acrylamide or other soluble non-ionic monomer.

Instead of the polymer being an emulsion at the time of incorporation of the active ingredient, the polymer can be an aqueous solution of a polymer that has been solubilised by volatile amine (preferably ammonia) and the amine is volatalised by heating the polymer during drying.

Thus an oil-in-water emulsion polymer containing acrylic acid or other anionic monomer may be converted into a solution by adding ammonia or other volatile amine and the polymer then converted back to a water-insoluble form by heating to drive off the ammonia. This is desirable when the polymer is to prevent release of the active ingredient except when the particles are exposed to external predetermined pH conditions. However when the purpose of putting the polymer into a less soluble form is primarily to reduce the hydrophilicity of the particles then it is unnecessary to start with an oil-in-water emulsion polymer. Instead, the polymer can be a polymer that has some degree of water solubility at pH below 6 (for instance polyacrylic acid) but which is much more soluble and hydrophilic when the carboxylic acid groups are neutralised.

In these circumstances, the polymer is a polymer of a water soluble monomer or monomer blend, generally being formed from anionic monomer as described above either alone or with water soluble non-ionic monomer; such as methacrylamide. Preferred polymers are formed from 50 to 100% (meth) acrylic acid and 0 to 50% acrylamide. Products made in this manner are of particular value when the active ingredient is a detergent enzyme since the partial or fully free acid form of the polymer is much less hydrophilic than the full salt form of the polymer and so gives better protection against ambient moisture during storage, but the polymer dissolves rapidly in wash liquor containing detergent, especially because such liquor is usually slightly alkaline.

The molecular weight of the water soluble polymer will be selected having regard to the concentration and solution viscosities that are required and, especially, the gel strength that is required in the final beads. If the molecular weight is too high in a solution polymer it can be difficult to form a stable dispersion of aqueous polymer particles containing a commercially useful concentration of active ingredient and so for many polymers the molecular weight should be below 1 million, often below 500,000. However higher molecular weights can easily be used when the polymer is an emulsion polymer. If the molecular weight is too low the final gel strength may be inadequate, even if the beads do have surface cross linking.

The polymers that are used in the invention may be unreactive polymers, i.e., polymers that cannot undergo any significant chain extension even though it may be possible to cause cross linking through pendant groups since any such cross linking does not usually result in any significant exotherm or other conditions that might damage the active ingredient. It is also possible to use a polymer that undergoes chain extension by addition polymerisation during the process provided this does not involve the presence of deleterious amounts of initiator, exotherm or other conditions that might damage the active ingredient. The risk of this can be minimised by ensuring that the reactive polymer already has a substantial chain length, for instance at least 50 and usually at least 100 carbon atoms in the chain. Depending upon the degree of unsubstitution in the reactive polymer, the final polymer may be linear or may be cross linked and, if cross linked, the polymeric matrix will then be swellable rather than soluble. Preferred reactive polymers are described in EP-A-0328321.

The polymer may undergo cross linking before, after or preferably curing its conversion to dry particles. For instance it is known that many polymers, especially those containing anionic groups, can undergo ionic cross linking if exposed to polyvalent metal compounds and so the inclusion of such compounds in the aqueous solution of polymer or in the non-aqueous liquid or both can result in cross linking. If the polyvalent metal compound is preferentially soluble in the non-aqueous liquid (for instance being aluminium isopropoxide or other polyvalent metal alkoxide) then the cross linking will be concentrated primarily at the surface of the particles. If the cross linking agent is preferentially soluble in the aqueous solution of polymer then the cross linking may occur substantially uniformly throughout the particles. Cross linking agents such as glutaraldehyde can be used with appropriate polymers. By appropriate selection of the type and amount of cross linking it is possible to control the physical properties of the particles. For instance it is possible to control the release of active ingredient from the particles and/or to increase the gel strength of the particles and/or to increase the hardness, or reduce the stickiness, of the surface of the particles. Also, if the cross linking is concentrated on the surface of the particles, the resultant particles tend to dissolve more rapidly into water.

In order to form the desired particles, the active ingredient is combined with the polymer solution or emulsion so as to form an aqueous phase containing the polymer and the active ingredient distributed substantially uniformly throughout the aqueous phase.

The concentration of the polymer in the aqueous composition containing polymer and active ingredient will depend on the viscosity of the solution or emulsion but is generally in the range 5 to 50%, typically 20 to 30%.

The active ingredient can be provided in solid form that is dismersed or dissolved into the polymer solution is or emulsion or it can be provided in liquid form, for instance as an aqueous solution or emulsion. In particular, when it is a biologically produced material, it can be provided in the form of a fermentation liquor or plant extract containing the material, as described in our copending application filed Ser. No. 07/398,057, Aug. 24, 1989 now U.S. Pat. No. 5,035,900. The aqueous phase can contain pigments, fillers or stabilisers, if required. For instance polyhydroxy compounds such as sucrose or propylene glycol can be introduced as stabilisers for enzymes.

The solution or emulsion is then dried to form the dry matrix by evaporating the continuous phase of the emulsion or the water of the solution. Before, during, or after this evaporation the composition must be shaped into the desired form. For instance the solution or emulsion can be dried while in bulk form, for instance while spread as a layer over a surface that is exposed to drying conditions, and can then be comminuted. Although the comminution will expose some active ingredient, the amount that is exposed will be low provided the dilution of active ingredient is low.

Another way of converting the solution or emulsion to a solid composition is by spray drying. The spray dried product can be a relatively fine powder and so conveniently it is converted into agglomerates or pellets in conventional manner, for instance by application of a binder.

When the active ingredient is a product produced from a fermentation broth, a preferred process can therefore comprise converting this broth into agglomerates by spray drying in the presence of a binder followed by agglomeration and, optionally coating the agglomerates in conventional manner, but the process is modified by using the emulsion or volatile amine solution of the defined polymer.

A preferred method of drying the solution or emulsion is to disperse it in a water immiscible liquid and then to dry the dispersion by azeotroping. The immiscible liquid is normally a water immiscible liquid that consists of or includes an appropriate hydrocarbon or other water immiscible, organic solvent that will form an azeotrope with water. The azeotroping is preferably conducted at temperatures below 100° C. and if the active ingredient is sensitive to elevated temperatures the azeotroping is preferably conducted under reduced pressure using a solvent such that the maximum temperature to which the dispersed particles are subjected is not more than 80° C. and preferably is always kept below 70° C. and preferably below 50° C., for instance as low as 30° C. Sodium sulphate or other suitable salt may be added to lower the necessary azeotroping temperature.

When the solution or emulsion is dispersed into an immiscible liquid, dispersion may be facilitated by the presence of a water-in-oil emulsifier and/of by the presence of an amphipathic polymeric stabiliser, for instance formed from hydrochilic and hydrophobic acrylic monomers. Suitable immiscible liquids, emulsifiers and stabilisers for this purpose are those that are conventional in reverse phase polymerisation and are described in for instance EP 128661 and 126528. The stabilisers described in GB 2,002,400 or, preferably, 2,001,083 or 1,482,515 are particularly preferred. If a polymer emulsion is being dispersed then the emulsifier that is used must not be such as to cause breakage of the polyomer-in-water emulsion.

The particle size of the aqueous droplets and the final particles can be controlled by choice of the amount of shear to which the dispersion is subjected, choice and amount of stabiliser and choice and amount of surfactant. When the end product is to be a stable dispersion in oil or other immiscible liquid it is preferred to use a water-in-oil emulsifier to promote the formation of small particles having a size below 10 μm, for instance below 3 μm. However when beads are required surfactant can be omitted and it is possible to make, for instance, beads having a size of at least 30 μm, generally at least 80 μm, preferably in the range 100 to 500 μm, although larger particles up to 1 or 2 mm can be provided.

The invention is of particular value when applied to the formation of powdered products either as agglomerated spray dried products or, preferably, azeotroped beads. When making the beads by azeotroping, the azeotroping is continued until the particles are sufficiently dry that they can be recovered from any residual immiscible liquid, for instance by conventional centrifuging or other filtration techniques. The particles can then be further dried if desired by extraction with acetone or other suitable organic liquid or, preferably, by exposure to warm air, generally as a fluidised bed.

The active ingredient may be any material that is required to be releasably trapped within a polymeric matrix and thus may be selected from synthetically produced materials, for instance, finely divided pigment, agriculturally active pesticides and other chemicals, and pharmaceutically active chemicals, and biologically-produced materials such as enzymes, fungi, spores, bacteria, cells and antibiotics. The invention is of particular value when the active ingredient is one that would interfere with or be damaged by monomer from which the polymer is made or would tend to be deactivated (either by evaporation or desensitisation) if excessed to exothermic polymerisation. The invention is therefore of particular value when the active ingredient is a sensitive material that is liable to be desensitised.

One particularly preferred type of active ingredient is a protease, especially an alkaline protease, of the type used in detergents, but other suitable enzymes for washing powders include amylases and lipases. For instance beads made by the invention can be included in washing powders and dispersions made by the invention can be included in liquid detergents.

Another active ingredient is a biologically active material that is to be protected from the acid pH that prevails in the stomach and which is to be released at the higher pH that prevails in the lower gastro intestinal tract. Although this can be an active ingredient that exerts an effect in the human or livestock through which it is passing, the active ingredient is preferably a biopesticide, bioherbicide or biofertiliser. An example is Bacillus Thurinaiensis toxin for killing lavae. With this, and with many other microbial products, the cells can be encapsulated either dead or alive because it is the toxic protein within the cell, rather than the living cell that is required. However in some instances it is desirable for the cell to be alive within the polymeric matrix in order that it can metabolise and multiply as soon as it is released from the matrix, for instance on a leaf surface, in the ground, or at some point in the alimentary canal.

The invention is of particular value when the active ingredient is an active ingredient that is to exert a pesticidal effect in the faeces of livestock since t is possible to formulate the polymeric matrix such that there is no release of the active ingredient as it passes through the animal but that there is release due to the exposure to ammonia that is formed in the faeces after they have been deposited by the livestock.

Thus an important aspect of the invention is the incorporation of a veterinary pesticide in a polymeric matrix that does not swell or dissolve when exposed to the pH conditions in the mouth (that can be close to pH 7) or elsewhere as it passes through the body of the animal or foul but which is solubilised or swollen upon exposure to the ammonia that is formed by natural degradation of the faeces after being deposited in the field or elsewhere. This is of value for killing or controlling flies and other insects that tend to feed of faeces and, in particular, for killing nematodes. Thus the active ingredient can be a fungal material of a nematode-destroying fungus, as discussed in WO88/06407.

The following are examples.

EXAMPLE 1

A copolymer of ethyl acrylate and methacrylic acid is made by oil-in-water emulsion polymerisation to a medium molecular weight and the polymer is dissolved in aqueous ammonia to give a 20% solution. The active ingredient (Bacillus Thuringisis) is dissolved or suspended in this solution in a polymer:active ingredient ratio by weight of 19:1.

The solution is stirred into a paraffinic oil in the presence of an amphipathic polymeric stabiliser formed from stearyl methacrylate, methyl methacrylate and methacrylic acid. The resultant dispersion is subjected to azeotropic distillation under reduced pressure such that the maximum temperature in the dispersion does not exceed about 50° C. The ammonia is driven off during this distillation to render the polymer insoluble in water. Once sufficient water has been taken off for the dispersed particles to be substantially dry to touch, they are separated from the remaining liquid by filtration and can then be further dried in the conventional manner. They have a particle size in the range 100 to 1,000 µm.

The resultant beads, when exposed to acidic conditions (for instance typical of those prevailing in the stomach) remain wholly unswollen and give substantially no release of the active ingredient. However when the beads pass into an area of higher pH, for instance as they pass further down the alimentary canal, they swell to start releasing their active ingredient and eventually or immediately dissolve totally.

EXAMPLE 2

A solution is formed of 640 g 25% emulsion at pH 4 of a copolymer of methacrylic acid and butyl acrylate and 160 g 5% detergent protease solution (i.e., 8 g dry weight enzyme and 160 g dry weight polymer) and its pH is adjusted to 7. 1600 g of a water immiscible liquid (solvent 41) and 53 g of a 15% solution inorganic solvent solution of an amphipathic polymeric stabiliser are charged to a 3 liter resin pot equipped with a mechanical stirrer and a Dean & Stark apparatus connected to a condenser and the aqueous phase is added and the mixture stirred for five minutes, leading to the formation of small bead droplets. The contents are then warmed to the chosen temperature, typically 45° C., and solvent and water azeotropically distilled by reducing the pressure to a value at which distillation occurs. The volume of water that is removed was observed and distillation was continued until no further water was collected.

The contents of the flask are cooled, the beads filtered, washed in acetone and dried in hot air.

The final product has 12 to 15% moisture content, is in the form of beads of regular almost spherical shape that are hard and free flowing and dissolved readily in cold and hot water. The beads have a narrow size range of approximately 250 to 500 µm and the product was substantially free of dust. The beads are insoluble and non-swelling in tap water but dissolved when exposed to water having pH 9.

EXAMPLE 3

To demonstrate the effect of small differences in pH, beads were made by the process of Example 1 or Example 2 and contained 1% Carbolan Blue (a water soluble dye) and 10% china clay (particle size 2–5 µm). The beads were exposed to an aqueous medium of gradually increasing pH.

The amount (%) released at different pH values was as follows:

| pH   | 6.26 | 7.18  | 7.21  | 7.38  | 7.43  | 7.5 |
|------|------|-------|-------|-------|-------|-----|
| dye  | 4.5  | 14.62 | 18.76 | 73.06 | 85.74 | 100 |
| clay | 0    | 2.3   | —     | —     | 3.0   | 100 |

This demonstrates that the release of soluble materials can be controlled by pH adjustment but that swelling of the matrix may allow some release slightly below the pH value at which major release occurs, whereas the release of insoluble materials (such as pigments and cellular materials) can be controlled so that substantially total release occurs over a very narrow pH range (typically below 0.2 or 0.1 pH units) with substantially no release at lower pH values.

EXAMPLE 4

The process of example 2 is repeated except that the copolymer emulsion is replaced by an equivalent amount of polymethacrylic acid as the 100% ammonium salt.

The final beads have the polymer mainly as the free acid polymer, especially near the surface. The beads dissolve rapidly in water when mixed into water with other detergent components.

As a comparison, when sodium polyacrylate is used in place of ammonium polyacrylate, the final beads have the polymer in the sodium form and they are less stable against loss of enzymic activity during storage, presumably because the polymer is more hydrophilic.

We claim:

1. A process for forming a particulate composition comprising particles comprising a dry matrix formed of an anionic matrix polymer through which an active ingredient is distributed, wherein the amount of polymeric material is at least 0.5 times the weight of active ingredient and is at least 50% of the weight of the matrix, the matrix polymer is soluble or swellable in water at a pH above 7 and is substantially insoluble and non-swellable in water at a lower pH, And the active ingredient is enzymes, fungi, spores, bacteria, cells or antibiotics, the process comprising:

providing an aqueous phase solution of a salt of the matrix polymer with ammonia whereby the matrix polymer is substantially water insoluble and non-swellable, dissolving or dispersing the active ingredient in the aqueous phase, forming a dispersion consisting essentially of the aqueous phase in water immiscible liquid, subjecting the dispersion to distillation and thereby evaporating water from the aqueous particles and forming solid particles of the matrix polymer having active ingredient distributed throughout, wherein ammonia of the salt present is evaporated during the distillation and the matrix polymer in salt form is thereby converted to its free acid form whereby the polymer is substantially water insoluble and non-swellable.

2. A process according to claim 1 in which the matrix polymer is formed from ethylenically unsaturated monomer comprising carboxylic monomer and said aqueous phase is said aqueous solution.

3. A process according to claim 1 in which the matrix polymer is formed of 50 to 100% by weight (meth)acrylic acid and 0 to 50% acrylamide.

4. A process according to claim 1 in which the amount of polymer is at least 7 times the amount of active ingredient and the polymer is at least 90% by weight of the matrix.

5. A process according to claim 4 in which the amount of polymer is 15 to 50 times the amount of the active ingredient.

6. A process according to claim 1 in which the active ingredient is enzymes.

7. A process according to claim 1 in which the particles are dry particles having a size of 30 µm.

8. A process according to claim 1 in which the particles are dry beads having a size of 100 µm to 2 mm.

9. A processing according to claim 1 in which the particles have a size of at least 30 µm, the active ingredient is a pesticide that is to be effective in animal faeces, the matrix does not release the active ingredient while the particles are in the mouth or passing through a cow, but the polymer does swell, with or without dissolving, sufficient to release the active ingredient when the particles are exposed to ammonia in the faeces.

10. A process according to claim 1 in which the active ingredient is an enzyme suitable for use in detergents and selected from the group consisting of protease, lipase and amylase.

11. A process for forming a particulate composition comprising a stable dispersion in hydrophobic liquid of particles having a size below 10 µm comprising a dry matrix formed of an anionic matrix polymer through which is distributed an enzyme suitable for use in detergents and selected from the group consisting of protease, lipase and amylase, wherein the amount of polymeric material is at least 0.5 times the weight of enzyme and is at least 50% of the weight of the matrix, the matrix polymer is soluble or swellable in water at a pH above 7 and is substantially insoluble and non-swellable in water at a lower pH, the process comprising:

providing an aqueous phase salt of the matrix polymer with ammonia whereby the matrix polymer is substantially water insoluble and non-swellable, dissolving or dispersing the enzyme in the aqueous phase, forming a dispersion consisting essentially of the aqueous phase in water immiscible liquid, subjecting the dispersion to distillation and thereby evaporating water from the aqueous phase and forming solid particles of the matrix polymer having enzymes distributed throughout, wherein the ammonia of the salt present is evaporated during said distillation and the matrix polymer in salt form is thereby converted to its free acid form whereby the polymer is substantially water insoluble and non-swellable.

* * * * *